United States Patent [19]

Gürtzgen et al.

[11] Patent Number: 5,380,898

[45] Date of Patent: Jan. 10, 1995

[54] PROCESS FOR PREPARING TRIMETHYLALUMINUM BY REACTING METHYLALUMINUM CHLORIDES WITH SODIUM IN SOLIDS REACTORS

[75] Inventors: Stefan Gürtzgen, Wuppertal; Jürgen Schneider; Rolf Schrader, both of Unna, all of Germany

[73] Assignee: Hoechst Aktiengesellschaft, Frankfurt am Main, Germany

[21] Appl. No.: 45,973

[22] Filed: Apr. 9, 1993

[30] Foreign Application Priority Data

Apr. 22, 1992 [DE] Germany .............. 4213202

[51] Int. Cl.⁶ .............................. C07F 5/06
[52] U.S. Cl. .............................. 556/187
[58] Field of Search ...................... 556/187

[56] References Cited

U.S. PATENT DOCUMENTS

| | | | |
|---|---|---|---|
| 2,619,330 | 11/1952 | Willems | 259/96 |
| 2,744,127 | 5/1956 | Ziegler et al. | 260/448 |
| 2,839,556 | 6/1958 | Ziegler et al. | 260/448 |
| 5,015,750 | 5/1992 | Tran et al. | 556/187 |

FOREIGN PATENT DOCUMENTS

| | | | |
|---|---|---|---|
| 0580631 | 8/1959 | Canada | 536/187 |
| 2363888 | 7/1975 | Germany | |
| 734541 | 8/1955 | United Kingdom | |
| 0980765 | 1/1965 | United Kingdom | 556/187 |

OTHER PUBLICATIONS

List DTB (Discotherm 20) Operating Instructions (Jun. 1989).

Organometallic Chemistry, H. Zeiss, Reinhold Publishing Corporation, N.Y., pp. 197–198 (1960).

Inorganic Chemistry and Radiochemistry, H. J. Emeleus, A. G. Sharpe, Academic Press, 1965, p. 269.

Primary Examiner—José G. Dees
Assistant Examiner—Porfirio Nazario-Gonzalez
Attorney, Agent, or Firm—Curtis, Morris & Safford

[57] ABSTRACT

The invention relates to a process for preparing trimethylaluminum from methylaluminum chlorides and sodium or magnesium which is characterized in that the components are reacted in a solids reactor.

12 Claims, 2 Drawing Sheets

FIG. I

PROCESS FOR PREPARING TRIMETHYLALUMINUM BY REACTING METHYLALUMINUM CHLORIDES WITH SODIUM IN SOLIDS REACTORS

RELATED APPLICATION

This application is based upon German application P42 13 202.9, filed Apr. 22, 1992, priority of which is claimed and, which is hereby incorporated herein by reference. Reference is also made to concurrently filed application Ser. No. 08/044/953 filed Apr. 9, 1993 in the names of Becker, Gürtzgen, Schneider and Schrader based upon German application P42 15 745.5, filed May 13, 1992; both of which are also hereby incorporated herein by reference.

FIELD OF THE INVENTION

The invention relates to a process for preparing trimethylaluminum from methylaluminum chlorides and sodium or magnesium which is characterized in that the components are reacted in a solids reactor.

BACKGROUND OF THE INVENTION

Trimethylaluminum (TMA) is increasingly attracting attention because of its many applications in the areas of semiconductors, aluminizing by electrodeposition, and catalysis in polyolefin production.

A great many methods of preparing trimethylaluminum are described in the literature, for example, in U.S. Pat. Nos. 2,744,127 and 2,839,556; Adv. Inorg. Chem. Radiochem. 7, 269 (1967); and Zeiss, Organomet. Chem., ACS Monograph No. 147, 197 (1960).

On the industrial scale, trimethylaluminum is usually produced by reduction of methylaluminum chlorides, and primarily dimethylaluminum chloride (DMAC), with molten metallic sodium, dispersed in an inert hydrocarbon such as Tetralin ® (tetrahydronaphthalene), n-decane, n-heptane, etc., according to the reaction equation

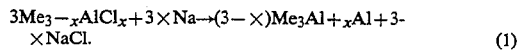

$$3Me_{3-x}AlCl_x + 3 \times Na \rightarrow (3-x)Me_3Al + xAl + 3-x NaCl. \quad (1)$$

The methylaluminum chlorides to be used include dimethylaluminum chloride (DMAC) and methylaluminum sesquichloride.

Because of passivation effects due to the deposition of reaction byproducts (NaCl Al) on the surface of the sodium, however, the yields are moderate (47 to 85 percent), and the trimethylaluminum obtained is contaminated by residues of the starting product dimethylaluminum chloride, and of the inert hydrocarbon which is often used in large amounts as a suspending agent. Besides, antipollution and industrial safety considerations make it advisable to dispense with readily flammable and toxicologically questionable solvents.

Using sodium in excess promotes the formation of complex alkyls, which reduces the yield still more:

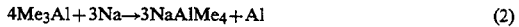

$$4Me_3Al + 3Na \rightarrow 3NaAlMe_4 + Al \quad (2)$$

In addition, reactor fouling as well as waste disposal and safety problems due to included sodium are observed. U.S. Pat. No. 5,015,750 relates to a process by which trimethylaluminum is obtained from methylaluminum chlorides and sodium in yields of about 90 percent without using sodium in excess. The product contains only about 0.03 percent chlorine and the synthesis requires considerably less suspending agent than comparable processes. However, such favorable results are obtained only in the presence of from 1 to 10 percent of catalysts such as alkali-metal and alkaline-earth fluorides, which must also be taken into consideration in connection with waste disposal.

Moreover, in the operating procedure there proposed, dimethylaluminum chloride and sodium are fed in simultaneously, the sodium being directed through the gas space onto the liquid surface. Now if the sodium is distributed by an agitator, for example, over the reactor wall above the liquid surface, the sodium will immediately react with the dimethylaluminum chloride, present in the gaseous phase. With this process repeating itself continually, considerable buildup will occur.

SUMMARY OF THE INVENTION

Surprisingly, it has now been found that these process-engineering drawbacks can be overcome by the use of solids reactors. In view of the low speed of rotation for which these reactors are designed, this was not to be expected since sufficiently uniform dispersion of the sodium or magnesium in the reaction mixture is known to have a great effect on the quality of the end product.

The invention thus relates to a process for preparing trimethylaluminum from methylaluminum chlorides and sodium or magnesium which is characterized in that the components are reacted in a solids reactor.

The invention further relates to a process for preparing trimethylaluminum which is characterized in that the methylaluminum chlorides, and preferably dimethylaluminum chloride, and sodium or magnesium are reacted at 100° to 190° C. and pressures of 0 to 5 bars for 4 to 8 hours in a solids reactor and the trimethylaluminum formed is removed by distillation.

Additional embodiments of the invention are disclosed below in or obvious from the following description and the claims.

DETAILED DESCRIPTION

Solids reactors within the meaning of the present invention are reactors which by reason of their design are capable of circulating mixtures with high solids contents or dry mixtures.

To cope with this task, a reactor must meet special requirements:

The agitator must be adapted to this particular task with respect to power and design, that is, the number and arrangement of the impellers mounted on the agitator shaft must assure sufficiently thorough mixing of the reactor content. In this connection, it is particularly important that the wall of the reactor and the surface of the agitator shaft be kept free of solids deposits and encrustation as otherwise homogeneous thorough mixing cannot be secured. In the case of the Discotherm apparatus DTB 20, manufactured by List in Switzerland, the use of which is preferred in accordance with the invention, this is accomplished by means of supplementary fixed built-in hooks in the reactor shell, which because of their closeness to the rotating impellers help to break up, in conjunction with the high shearing stresses in this region, any agglomerates forming during the reaction. Moreover, it will be of advantage if not only the reactor wall but also the agitator shaft can be heated since this will minimize encrustation and buildup of deposits.

The dimethylaluminum chloride used as a starting material in the process of the invention, as well as methylaluminum sesquichloride, are products of commerce.

As magnesium, the commercial powdered grades are used, preferably those with a purity better than 99 percent and a particle size not over 100μ, and more particularly under 75μ.

Figure 1:
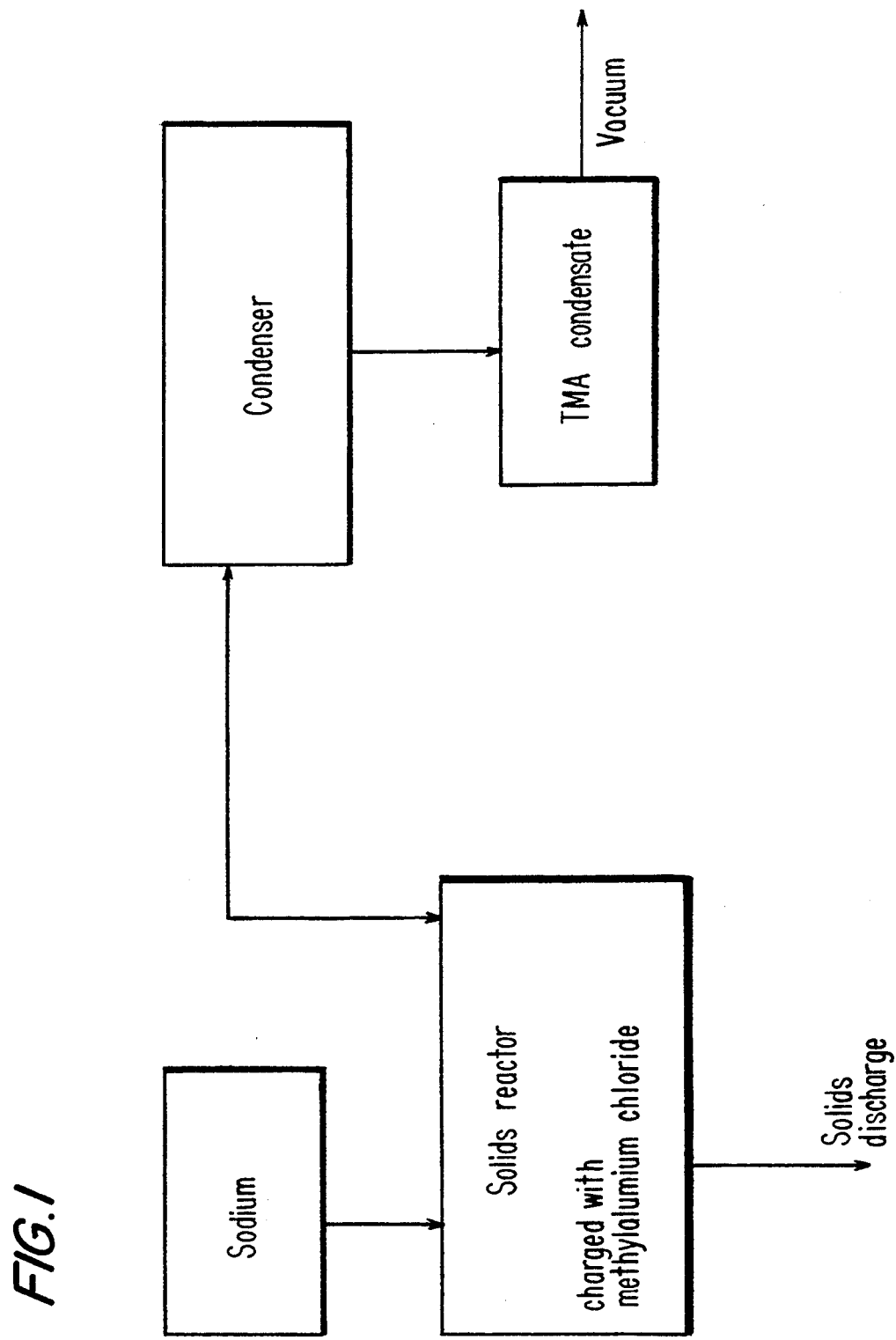
FIGS. 1 and 2 are process flow charts for using sodium and methylaluminum chloride (FIG. 1) and for using methylaluminum chloride and magnesium (FIG. 2).

Referring to FIG. 1, to carry out the reaction, the methylaluminum chlorides are introduced into the reactor, purged with an inert gas, as initial charge and heated with stirring to reaction temperatures of 100° to 190° C., and preferably 120° to 150° C. The sodium is then fed in continuously or in portions in solid or preferably molten form, and the reaction is continued at 120° to 150° C. for 3 to 6 hours, and preferably for about 4 hours. The total pressure (sum of the partial pressures of the methylaluminum chlorides and the trimethylaluminum, boiling point 126°–127° C.) building up because of the temperature is maintained during the reaction period. The trimethylaluminum formed is then distilled off, pressures not higher than $10^{-3}$ bars being advantageous for the complete removal of the trimethylaluminum.

During this phase, the reaction mixture undergoes drying to a solids content of approximately 100 percent. The powdered residue is largely discharged through the discharge pipe fitting. (FIG. 1.) Any residue then remaining will have no adverse effect on the reaction and may therefore be left in the reactor, which can then be charged anew as often as desired without further cleaning.

The trimethylaluminum obtained after distillation is of high purity and as a rule requires no aftertreatment since in accordance with the invention the reaction is carried out without the suspending agents normally needed.

While suspending agents may be used, their use in the solids reactors employed generally entails only drawbacks since they have an adverse effect on the purity of the distilled product and since the residues are then increased and result in higher disposal costs.

In accordance with the invention, sodium is used in an excess of up to 10 mole percent, based on the stoichiometric amounts. Larger excesses are undesirable from the process-engineering standpoint because of the side reactions which occur and because of the metallic sodium remaining in the distillation residue. Magnesium is used in an excess of up to 60 mole percent, and preferably of from 20 to 50 mole percent, based on the stoichiometric amounts. For the sake of shorter reaction periods, the excess should be limited to the range given above.

In accordance with the invention, liquid sodium is preferably used in an excess of from 0 to 5 mole percent, based on the stoichiometric amounts.

Figure 2:
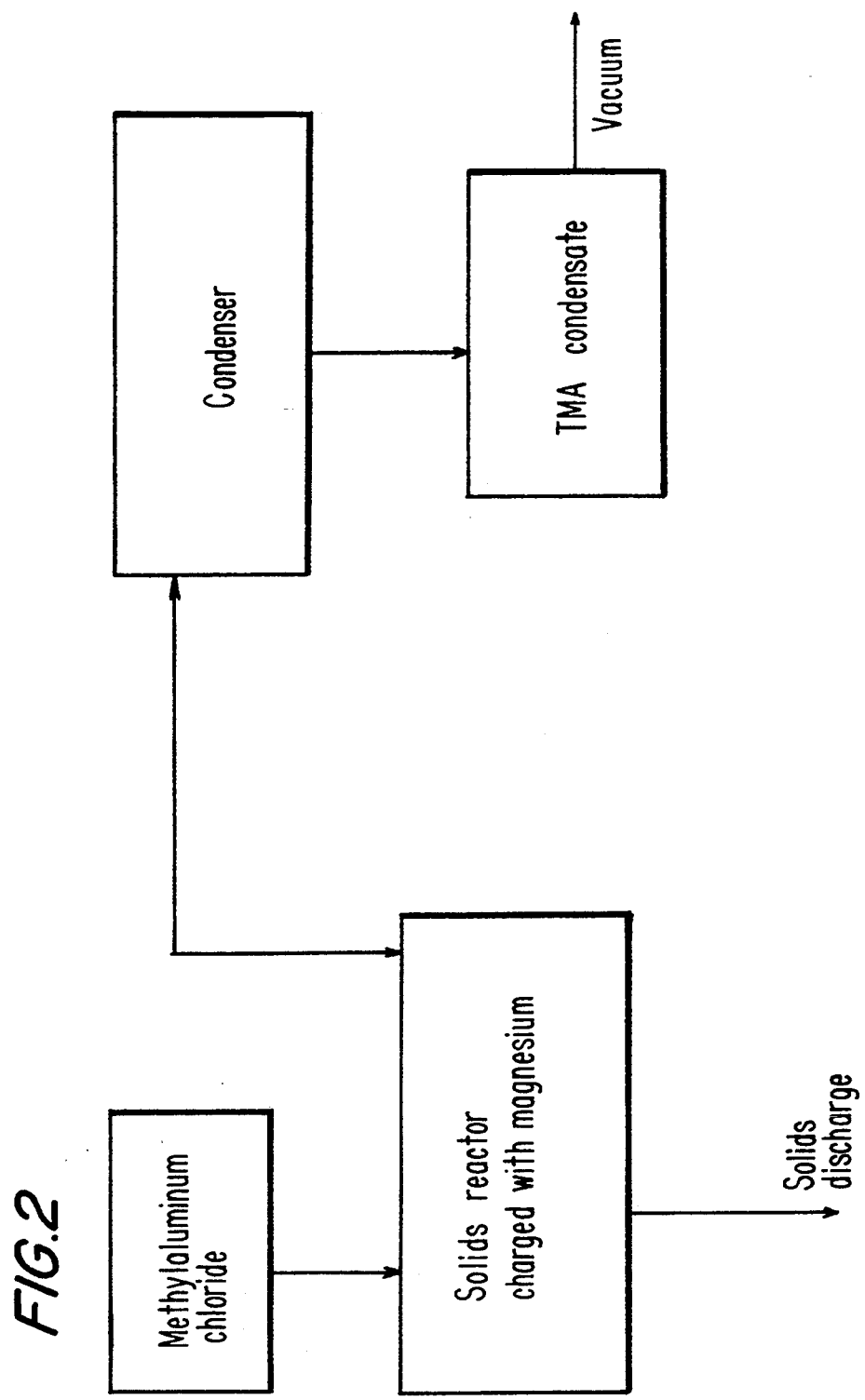

With reference to FIG. 2, when metallic magnesium is used, the magnesium powder is introduced as initial charge into the solids reactor, which has first been purged with an inert gas, and then heated wit stirring to reaction temperatures of 100° to 190° C., and preferably 140° to 180° C. The dimethylaluminum chloride is then fed in, preferably continuously. The reaction is continued for 3 to 6 hours at the total pressure which comes to prevail, and the reaction product is isolated in conformity with the conditions set forth above.

The reaction is preferably carried out at temperatures of from 120° to 180° C. It has been found that when stoichiometric amounts of sodium or magnesium are used, higher temperatures and/or longer reaction periods are generally required for optimum conversion. When magnesium is used, the reaction temperatures should be higher and the reaction periods longer than those in the range preferred for sodium.

The following examples are given by way of illustration only and are not to be considered as limitations of the present invention, many apparent variations of which are possible without departing from the spirit and scope thereof.

EXAMPLES

Example 1

The reactor (Discotherm DTB 20) purged with nitrogen was charged with 9.04 kg of dimethylaluminum chloride (DMAC), which was then heated to 120° C. With the agitator shaft of the reactor rotating (at 8 rpm), 2.46 kg of molten sodium was added in ten portions over a period of 140 minutes. The reactor temperature during the sodium addition was 121°–131° C. The contents of the reactor were then heated to 150° C. and maintained at that temperature for 4 hours. During this addition and the continued reaction, an overpressure of up to 3 bars was building up in the reactor. To separate the trimethylaluminum (TMA) formed from the reaction mixture, the pressure in the reactor was then reduced at reaction temperature to normal pressure, the escaping TMA vapor being liquefied in a condenser located downstream and collected in a receiver. The further TMA isolation was carried out by evaporation in a vacuum of up to 1 millibar and at 140°–150° C.

Yield: 4.1 kg of TMA distillate = 87.3% of theory

| | |
|---|---|
| Chlorine content (% Cl): | 0.0 |
| Aluminum content (% Al): | 37.1 |

The dry residue (approximately 100% solids content) was cooled to room temperature and discharged through the discharge pipe fitting.

Example 2

The same procedure was followed as in Example 1, except that the sodium was added continuously.

Yield: 4.3 kg of TMA distillate = 91.6% of theory

| | |
|---|---|
| % Cl: | 0.0 |
| % Al: | 37.2 |

Example 3

The same procedure was followed as in Example 1, except that a cycle of five successive individual batches (without intermediate cleaning of the reactor) was run. Result of 5th individual batch:

Yield: 4.15 kg of TMA distillate = 88.4% of theory

| | |
|---|---|
| % Cl: | <0.05 |
| % Al: | 37.1 |

Having thus described in detail the preferred embodiments of the present invention, it is to be understood that the invention defined by the appended claims is not to be limited by particular details set forth in the above description as many apparent variations thereof are possible without departing from the spirit or scope of the present invention.

What is claimed is:

1. A process for preparing trimethylaluminum from reactants comprising methylaluminum chloride and sodium or magnesium, the process comprising contacting the reactants under reaction conditions in a solids reactor.

2. A process for preparing trimethylaluminum according to claim 1, wherein the reaction conditions include temperature of about 100° to about 190° C. and a reaction time of about 3 to about 8 hours in the solids reactor and, the process further comprises removing the trimethylaluminum formed by distillation.

3. A process according to claim 1, wherein the reactants include an excess of sodium of up to 10 mole percent, based on stoichiometric amounts, and, the reaction conditions include temperature of about 120° to about 180° C.

4. A process according to claim 2, wherein the reactants include an excess of sodium of up to 10 mole percent, based on stoichiometric amounts, and, the reaction conditions include temperature of about 120° to about 180° C.

5. A process according to claim 1, wherein the reactants include an excess of magnesium of up to 60 mole percent, based on stoichiometric amounts, and, the reaction conditions include temperature of about 140° to about 150° C.

6. A process according to claim 2, wherein the reactants include an excess of magnesium of up to 60 mole percent, based on stoichiometric amounts, and, the reaction conditions include temperature of about 140° to about 150° C.

7. A process according to claim 1, wherein the methylaluminum chloride is dimethylaluminum chloride.

8. A process according to claim 2, wherein the methylaluminum chloride is dimethylaluminum chloride.

9. A process according to claim 3, wherein the methylaluminum chloride is dimethylaluminum chloride.

10. A process according to claim 4, wherein the methylaluminum chloride is dimethylaluminum chloride.

11. A process according to claim 5, wherein the methylaluminum chloride is dimethylaluminum chloride.

12. A process according to claim 6, wherein the methylaluminum chloride is dimethylaluminum chloride.

* * * * *

UNITED STATES PATENT AND TRADEMARK OFFICE
CERTIFICATE OF CORRECTION

PATENT NO. : 5,380,898
DATED : January 10, 1995
INVENTOR(S) : Gurtzen, et. al.

It is certified that error appears in the above-indentified patent and that said Letters Patent is hereby corrected as shown below:

Title page, item [73], Assignee: should read--Witco GmbH, Bergkamen, Germany--.

Signed and Sealed this

Seventh Day of May, 1996

Attest:

BRUCE LEHMAN

Attesting Officer

Commissioner of Patents and Trademarks